United States Patent
Osawa et al.

(10) Patent No.: US 11,318,084 B2
(45) Date of Patent: *May 3, 2022

(54) ELASTOMER

(71) Applicant: SHISEIDO COMPANY, LTD., Tokyo (JP)

(72) Inventors: Tomo Osawa, Yokohama (JP); Ayano Matsuo, Yokohama (JP); Yuji Sonoyama, Yokohama (JP); Tomoko Ikeda, Yokohama (JP); Shun Kubota, Yokohama (JP); Mao Hitomi, Yokohama (JP); Takuya Hiruma, Yokohama (JP); Tetsuya Kanemaru, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 591 days.

This patent is subject to a terminal disclaimer.

(21) Appl. No.: 16/305,474

(22) PCT Filed: May 29, 2017

(86) PCT No.: PCT/JP2017/019972
§ 371 (c)(1),
(2) Date: Nov. 29, 2018

(87) PCT Pub. No.: WO2017/209077
PCT Pub. Date: Dec. 7, 2017

(65) Prior Publication Data
US 2021/0228472 A1    Jul. 29, 2021

(30) Foreign Application Priority Data

May 31, 2016 (JP) .............. JP2016-108740

(51) Int. Cl.
| | |
|---|---|
| *A61K 8/898* | (2006.01) |
| *A61K 8/81* | (2006.01) |
| *A61K 8/19* | (2006.01) |
| *A61Q 1/12* | (2006.01) |
| *A61K 8/891* | (2006.01) |

(52) U.S. Cl.
CPC ............ *A61K 8/898* (2013.01); *A61K 8/19* (2013.01); *A61K 8/81* (2013.01); *A61K 8/891* (2013.01); *A61Q 1/12* (2013.01); *A61K 2800/624* (2013.01)

(58) Field of Classification Search
CPC . A61K 8/898; A61K 8/19; A61K 8/81; A61K 8/891; A61K 2800/62; A61Q 1/12
See application file for complete search history.

(56) References Cited

U.S. PATENT DOCUMENTS

| | | | |
|---|---|---|---|
| 2011/0027213 A1 | 2/2011 | Kamei et al. | |
| 2012/0082633 A1* | 4/2012 | Kinoshita | ............ A61K 8/8152 424/70.28 |

FOREIGN PATENT DOCUMENTS

| | | |
|---|---|---|
| JP | 2004-182729 | 7/2004 |
| JP | 2005-53736 | 3/2005 |
| JP | 2006-028087 | 2/2006 |
| JP | 2007-277167 | 10/2007 |
| JP | 2007-277415 | 10/2007 |
| JP | 2007-302800 | 11/2007 |
| JP | 2008-184399 | 8/2008 |
| JP | 2009-179606 | 8/2009 |
| JP | 2010-163375 A | 7/2010 |
| JP | 2011-026485 A | 2/2011 |
| JP | 2013-49658 | 3/2013 |
| JP | 2016-060720 | 4/2016 |
| JP | 2019-006715 | 1/2019 |
| WO | WO 97/30934 | 8/1997 |
| WO | WO 2017/209077 | 12/2017 |

OTHER PUBLICATIONS

Database WPI, Week 201633, Thomson Scientific, London, GB; AN 2016-25419M & JP 2016 060720 A (Narisu Keshohn KK) Apr. 25, 2016 (Apr. 25, 2016).
Database WPI, Week 200615, Thomson Scientific, London, GB; AN 2006-140396 & JP 2006 028087 A (Hoyu KK) Feb. 2, 2006 (Feb. 2, 2006).
EP 17806632.0, Extended European Search Report dated Dec. 10, 2019, 7 pages—English.
PCT/JP2017/019972, ISR and Written Opinion dated Jun. 20, 2017, 6 pages—Japanese, 7 pages—English.
KR 10-2018-7037845, Office Action dated May 4, 2021, 8 pages—English, 7 pages—Korean.
PCT/JP2018/041235, International Search Report and Written Opinion dated Feb. 5, 2019, 8 pages—Japanese, 4 pages—English.
PCT/JP2017/019972 filed May 29, 2017.
JP 2016-108740 filed May 31, 2016.
U.S. Appl. No. 16/765,695, filed May 20, 2020.

* cited by examiner

Primary Examiner — Jianfeng Song
(74) Attorney, Agent, or Firm — Andrew F. Young; Nolte Lackenbach Siegel

(57) ABSTRACT

Provided is an elastomer that improves the skin feel of an inorganic powder. The elastomer according to the present invention is an elastomer comprising: (A) an amino group-containing silicone polymer; and (B) a carboxyl group-containing silicone polymer or a carboxyl group-containing acrylamide polymer, wherein a molar ratio Y/X between amino groups and carboxyl groups is within a range of 0.1 to 1.2, wherein Y denotes the molar amount of carboxyl groups contained in the component (B), and X denotes the molar amount of amino groups contained in the component (A).

6 Claims, No Drawings

ELASTOMER

CROSS REFERENCE TO RELATED APPLICATIONS

This application relates to and claims priority from PCT Ser. No.: PCT/JP2017/019972 filed May 29, 2017, the entire contents of which are incorporated herein by reference, which in turn relates to and claims the priority of Japanese Patent Application No. 2016-108740 filed on May 31, 2016, which is also fully incorporated herein by reference.

BACKGROUND OF THE INVENTION

Field of the Invention

The present invention relates to elastomers and particularly relates to an elastomer that is particularly used to coat an inorganic powder to improve a sense of the coated inorganic powder therewith when applied on skin.

Background

Powders for makeup cosmetics such as foundation and makeup base are treated in various ways to provide the functions required for the makeup cosmetics.

For example, a powder is known in which the surface of a base powder is coated with a hydrophobizing agent and a polymer containing acrylamide monomers, having a specific structure (such as 11-methacrylamidoundecanoic acid), as a composition monomer thereof in order to achieve high hydrophobicity and improve washability (Patent Literature 1).

Concerning attempts to provide a powder cosmetic, in particular a powder makeup cosmetic such as foundation or makeup base, which has a high ability to allow makeup to last longer (prevent makeup from coming off), it is known that the incorporation of a particular treated powder provides a powder makeup cosmetic having a high ability to allow makeup to last longer (prevent makeup from coming off) (Patent Literature 2).

RELATED PRIOR ART DOCUMENTS

Japanese Patent Publication No. 2007-277167
Japanese Patent Publication No. 2008-184399

ASPECTS AND OBJECTS OF THE INVENTION

Problem to be Solved by the Invention

However, a treated inorganic powder as taught in Patent Literature 1 or 2 has a problem in that when a cosmetic containing the treated inorganic powder is applied to skin, the cosmetic may give frictional feel and unpleasant powdery sense to the skin.

The present invention has been made in view of such circumstances, and an object of the present invention is to improve the skin sense due to an inorganic powder along with imparting moisture and eliminating a powdery sense due to the inorganic powder by coating the inorganic powder with a specific elastomer. And another object of the present invention is to provide an inorganic powder coated with the specific elastomer in the cosmetic, which is superior to prevent the cosmetic from falling while applying.

Means to Solve the Problem

As a result of intensive investigations aimed at solving the above problem, the present inventors have found that a composition having elastomeric properties prepared by combining an amino group-containing silicone polymer (modified amino silicone polymer) with a carboxyl group-containing silicone polymer or a carboxyl group-containing acrylamide polymer can, when used to coat an inorganic powder, improve the skin feel of the inorganic powder and impart moisture, non-powdery feel thereto. The present inventors have also found that the cosmetic is well prevented from falling by using such an inorganic powder coated with the elastomer in a cosmetic. The present inventors have completed the present invention based on these findings.

That is, the elastomer according to the present invention is an elastomer comprising:
(A) an amino group-containing silicone polymer; and
(B) a carboxyl group-containing silicone polymer or a carboxyl group-containing acrylamide polymer, wherein a molar ratio (mol B)/(mol A) between amino groups and carboxyl groups is 0.1 to 1.2, wherein (mol B) denotes the molar amount of carboxyl groups contained in the component (B), and (mol A) denotes the molar amount of amino groups contained in the component (A).

It is preferable that the surface of an inorganic powder (C) is coated with the elastomer.

It is preferable that the amount of the elastomer in the elastomer-coated inorganic powder is 0.5 to 20% by mass relative to the amount of the inorganic powder (C).

It is preferable that the inorganic powder (C) in the elastomer-coated inorganic powder is talc, mica, synthetic phlogopite iron, sericite, barium sulfate, kaolin, titanium oxide, zinc oxide, or iron oxide.

It is preferable that the elastomer-coated inorganic powder is incorporated in a cosmetic.

It is also preferable that the surface of an organic powder (D) is coated with the elastomer.

A method of producing the elastomer-coated inorganic powder preferably comprises the steps of: mixing the inorganic powder (C) with the carboxyl group-containing silicone polymer or carboxyl group-containing acrylamide polymer (B) to produce a first mixture; and mixing the first mixture with the amino group-containing silicone polymer (A) to a second mixture and heating a second mixture.

A method of producing the elastomer-coated inorganic powder preferably comprises the steps of: mixing the inorganic powder (C) with the amino group-containing silicone polymer (A) to produce a third mixture; and mixing the third mixture with the carboxyl group-containing silicone polymer or carboxyl group-containing acrylamide polymer (B) to produce a fourth mixture and heating the fourth mixture.

A method of producing an elastomer-coated inorganic powder-containing cosmetic preferably comprises the step of further mixing the elastomer-coated inorganic powder with an oil component other than the components (A) and (B).

Effect of the Invention

The present invention provides a novel elastomer. An inorganic powder is coated with the novel elastomer, so that the coated inorganic powder attains improving skin senses and moistening senses with non-powdery feel. Additionally, the use of the inorganic powder coated with the present elastomer provides a cosmetic with providing excellent stability therefor and preventing well falling.

SUMMARY AND BEST MODE FOR CARRYING OUT THE INVENTION

Hereinafter, the present invention will be described in detail.

An elastomer according to the present invention is produced by mixing an amino group-containing silicone polymer and a carboxyl group-containing silicone polymer and heating the resulting mixture. The constitutional components of the present invention will be described first.

(A) Amino Group-Containing Silicone Polymer (Silicone Polymer Comprising an Amino Group and Related in the Molecule Thereof)

The amino group-containing silicone polymer (A) used in the present invention is a side chain amino-modified silicone represented by the following general formula (1).

[General Formula 1]

$$CH_3-Si(CH_3)_2-O-[Si(CH_3)(X)-O]_m-[Si(CH_3)(RNHR'NH_2)-O]_n-Si(CH_3)_2-CH_3 \quad (1)$$

wherein X is an alkyl group having 1 to 18 carbons, and R and R' are respectively an alkyl group.

In the general formula (1), m is preferably 20 to 2000 to provide the elastomer with a suitable hardness. Whereas, when m is less than 20, the elastomer may not be formed, and when m is more than 2000, handling and production thereof may become difficult, so that the results are not preferable.

In the general formula (1), n is preferably 1 to 100 to provide the elastomer with a suitable hardness. Whereas, when n is less than 1, the elastomer may not be formed and when n is more than 100, the elastomer may be excessively hard, so that the results are not preferable.

In the general formula (1), R is suitably an alkyl chain, and particularly, a propyl group is preferred in terms of mass production efficiency.

In the general formula (1), R' is suitably an alkyl chain, and particularly, an ethyl group is preferred in terms of mass production efficiency.

The amino group equivalent of the amino group-containing silicone polymer (A) is preferably 500 g/mol to 20000 g/mol to provide the resulting elastomer with a suitable hardness. Whereas when the amino group equivalent is less than 500, the elastomer may be excessively hard, and when the amino group equivalent is more than 20000, the elastomer may not be formed, so that the results are not preferable.

Examples of commercially-available products of the amino group-containing silicone polymer (A) include: KF-8004, KF-8005S, and KF-867S (available from Shin-Etsu Chemical Co., Ltd.); XF42-B1989 (available from Momentive Performance Materials Inc.); ADM 1650 and ADM 1370 (available from Wacker Asahikasei Silicone Co., Ltd.); and SF 8452C and SS 3551 (available from Dow Corning Toray Co., Ltd.).

The "amino group equivalent" refers to a value indicating the weight of an amino group-containing substance per mole of amino groups.

(B) Carboxyl Group-Containing Silicone Polymer and Carboxyl Group-Containing Acrylamide Polymer The carboxyl group-containing silicone polymer (B) used in the present invention is a side chain carboxyl-modified silicone having a carboxyl group equivalent of 1000 g/mol to 40000 g/mol and represented by the general formula (2) below.

The carboxyl group-containing acrylamide polymer (B) used in the present invention is a side chain carboxyl-modified acrylamide polymer having a carboxyl group equivalent of 200 g/mol to 1000 g/mol and represented by the general formula (3) below.

The "carboxyl group equivalent" refers to a value indicating the weight of a carboxyl group-containing substance per mole of carboxyl groups.

The general formula (2) is represented by the following general formula (2).

[General Formula (2)]

$$CH_3-SiO(CH_3)_2-[SiO(R^1)(R^2)]_y-Si(CH_3)_2-CH_3 \quad (2)$$

wherein R1 and R2 each denote a methyl group or a group represented by carboxy N-alkylpyrrolidone carboxylic acid group represented by the formula (4)] below, the number of the groups is 1 to 100 per molecule, and y represents an integer of 1 to 50000.

[Formula 4]

N-(CH$_2$)$_3$-pyrrolidone with CO$_2$H substituent

The general formula (3) is represented by the following polymer structure.

[General Formula 3]

$$\left( -CH_2-CH(C(=O)NH-C(CH_3)_2-CH_2-SO_3^-Na^+)- \right)_m \left( -CH_2-C(CH_3)(C(=O)NH-(CH_2)_{11}-COOH)- \right)_n \quad (3)$$

wherein m/(m+n)=0 to 0.5.

Examples of commercially-available products of the carboxyl group-containing silicone polymer represented by the general formula (2) include SENSASIL PCA (available from Croda, Inc.).

The carboxyl group-containing acrylamide polymer represented by the general formula (3) can be synthesized using a known method.

A specific example is 12-methacrylamidododecanoic acid (MAD)/2-acrylamido-2-methylpropanesulfonic acid (AMPS) copolymer (90/10), which was synthesized as follows.

18.50 g (65.37 mmol) of 12-methacrylamidododecanoic acid (MAD), 1.50 g (7.24 mmol) of 2-acrylamido-2-methylpropanesulfonic acid (AMPS, available from Sigma-Aldrich Japan K.K.), 0.29 g (7.25 mmol) of sodium hydroxide, and 0.30 g (1.83 mmol) of azobisisobutyronitrile (available from Nacalai Tesque, Inc.) were dissolved in 60.0 g of methanol. The azobisisobutyronitrile was recrystallized from methanol according to an ordinary method before use. The solution was degassed by bubbling with argon for 60 minutes, after which the container containing the solution was capped with a septum and heated at 60° C. for 20 hours to allow polymerization to proceed. After the completion of the polymerization reaction, the reaction solution was added dropwise into a largely excessive amount of diethyl ether, and the resulting precipitate was collected by suction filtration. The collected precipitate was then dried under reduced pressure to give 15.2 g of a random MAD/AMPS copolymer (90/10) (yield: 75.1%). The weight-average molecular weight was 50000.

The carboxyl group equivalent of the component (B) is preferably 200 to 40000, because in this case the resulting elastomer has a suitable hardness. It is not preferable that the carboxyl group equivalent be less than 200, because in this case the elastomer may be excessively hard. It is not preferable that the carboxyl group equivalent be more than 40000, because in this case the elastomer may not be formed.

A molar ratio Y/X between amino groups of the amino group-containing silicone polymer (A) and carboxyl groups of the carboxyl group-containing silicone polymer or carboxyl group-containing acrylamide polymer (B) must be 0.1 to 1.2, wherein Y denotes the molar amount of carboxyl groups contained in the component (B), and X denotes the molar amount of amino groups contained in the component (A). This ratio is more preferably 0.1 to 0.8. It is not preferable that the ratio be less than 0.1, because in this case the elastomer may not be formed. It is not preferable that the ratio be more than 1.2, because in this case the elastomer may not be formed.

(C) Inorganic Powder

When an inorganic powder (C) is coated with the elastomer of the present invention, the coated inorganic powder attains improving skin sense and providing moisture without powdery feel. With the use of the inorganic powder coated with the elastomer in a cosmetic, a cosmetic that is not falling and stable with an excellent impact can be obtained.

The inorganic powder (C) used in the present invention is selected from powder materials usable in cosmetics.

Examples of inorganic powder include talc, boron nitride, sericite, natural mica, calcined mica, integrated mica, integrated sericite, alumina, mica, kaolin, bentonite, smectite, calcium carbonate, magnesium carbonate, calcium phosphate, anhydrous silicic acid, magnesium oxide, tin oxide, iron oxide, yttrium oxide, chromic oxide, titanium oxide, zinc oxide, cerium oxide, aluminum oxide, magnesium oxide, chromium hydroxide, prussian blue, ultramarine, calcium phosphate, aluminum hydroxide, barium sulfate, magnesium sulfate, silicic acid, magnesium aluminum silicate, silicic acid calcium, silicic acid barium, magnesium silicate, aluminum silicate, silicic acid strontium, silicon carbide, magnesium fluoride, tungstic acid metal salt, magnesium aluminate, magnesium aluminometasilicate, chlorohydroxy aluminum, clay, zeolite, hydroxy apatite, ceramic powder, spinel, mullite, cordierite, aluminum nitride, titanium nitride, silicon nitride, a lantern, samarium, tantalum, terbium, europium, neodymium, Mn—Zn ferrite, Ni—Zn ferrite, silicon carbide, titanic acid cobalt, barium titanate, titanic acid iron, lithium cobalt chitanate, aluminic acid cobalt, antimony containing tin oxide, tin containing indium oxide, magnetite, aluminum powder, gold powder, silver powder, platinum powder, copper powder, noble metal colloid, iron powder, zinc powder, cobalt blue, cobalt violet, cobalt green, lower titanium oxide, titanium oxide particulate, butterfly-like barium sulfate of, petal-like zinc oxide, tetrapod-like zinc oxide, zinc oxide particulate, mica coated with titanium oxide, mica coated with titanium oxide, silica coated with titanium oxide, integrated mica coated with titanium oxide, talc coated with titanium oxide, silica coated with zinc oxide, pigmentation mica coated with titanium oxide, mica titanium coated red oxide, mica titanium coated red ocher and black iron oxide, mica titanium coated carmine, and mica titanium coated iron blue pigments.

The amount of the elastomer with which the inorganic powder is coated is 0.5 to 20% by mass, more preferably 1 to 15% by mass, relative to the amount of the inorganic powder. It is not preferable that the amount of the elastomer to be incorporated be more than 20% by mass, because in this case fusing of the inorganic powder or decrease in formability of the powder cosmetic may occur. It is not preferable that the amount of the elastomer to be incorporated be less than 0.5% by mass, because in this case the feel-improving effect may not be obtained.

Examples of commercially-available products of the inorganic powder include: IRIODIN® series, TIMIRON® series, COLORONA® series, DICHRONA® series, XIRONA® series, and RONASTAR® series of MERCK KGaA; DESERTREFLECTIONS series, TIMICA series, FLAMENCO series, CLOIZONNE series, DUOCROME series, GEMTONE series, CELLINI series, MEARLMAID series, REFLECKS series, CHROMA-LITE series, and COSMICA series of BASF SE; PRESTIGE® series, VISIONAIRE® series, and MIRAGE series of ECKART GmbH; METASHINE® of Nippon Sheet Glass Co. Ltd.; PROMINENCE® of NIHON KOKEN KOGYO CO., LTD.; Cosmetica White Pearl series and Sharon Pear 1 series of CQV Co., Ltd.; and Precioso White Peartescent Pigments of Taizu. Other examples of the inorganic powder include: effect pigments such as aluminum flakes, silica flakes, alumina flakes, and glass flakes; colcothar-coated mica; carmine; titanium oxide-coated sodium/calcium borosilicate; titanium oxide-coated calcium/aluminum borosilicate; bismuth oxychloride; fish scale flakes; stainless steel powder; tourmaline powder; powders obtained by crushing precious stones such as sapphire and ruby; mango violet; glass fibers; carbon fibers; silicon carbide fibers; alumina fibers; β-wollastonite; Zonolite; potassium titanate fibers; aluminum borate fibers; basic magnesium sulfate fibers; and silicon nitride fibers.

(D) Organic Powder

The elastomer of the present invention can be also used to coat an organic powder (D).

The organic powder (D) used in the present invention is selected from powder materials usable in cosmetics.

Examples of the component (D) include: organic powders such as silicone elastomer powder, silicone powder, silicone resin-coated silicone elastomer powder, polyamide resin powder (nylon powder), polyethylene powder, polymethyl methacrylate powder (such as methyl methacrylate crosspolymer), polystyrene powder, styrene-acrylic acid copolymer resin powder, benzoguanamine resin powder, polytetrafluoroethylene powder, and cellulose powder; organic pigments such as zirconium lakes, barium lakes, and aluminum lakes (for example, organic pigments such as Red No. 201, Red No. 202, Red No. 204, Red No. 205, Red No.

220, Red No. 226, Red No. 228, Red No. 405, Orange No. 203, Orange No. 204, Yellow No. 205, Yellow No. 401, and Blue No. 404).

An elastomer-coated inorganic powder according to the present invention can be obtained through a step of mixing the inorganic powder (C) with the amino group-containing silicone polymer (A) and a step of adding the carboxyl group-containing silicone polymer (B) and heating the resulting mixture.

The elastomer-coated inorganic powder can be obtained by a known method of producing a coated powder. Specifically, for example, talc and the amino group-containing silicone polymer (A) are placed in a Henschel mixer and mixed at a low speed for 10 minutes. The carboxyl group-containing silicone polymer (B) is then added, followed by mixing at a low speed for 10 minutes and then by heating. In this manner, the elastomer-coated inorganic powder according to present invention can be obtained.

The order of addition of the component (A) and component (B) may be reversed to obtain the elastomer-coated inorganic powder according to the present invention.

An elastomer-coated organic powder can also be obtained by a known method of producing a coated powder.

The elastomer-coated inorganic powder of the present invention has good in-use feel and is therefore preferably incorporated in a cosmetic. Examples of the cosmetic include, but are not limited to, powder cosmetics, W/O emulsion cosmetics, O/W emulsion cosmetics, and oily cosmetics.

<Dry Production Method>

An inorganic powder component, an oil component, and other components are first mixed using a Henschel mixer, and the mixture is crushed twice using a pulverizer. The resulting mixture is charged into a middle-sized dish made of resin and subjected to dry press forming according to a known method. In this manner, a solid powder cosmetic containing the elastomer-coated inorganic powder of the present invention can be obtained.

<Other Production Methods>

Known methods can be used as the method of producing a cosmetic containing the elastomer-coated inorganic powder of the present invention. For example, such a cosmetic can be suitably obtained by a production method described in Japanese Patent No. 5422092 in which a slurry prepared using a volatile solvent is dried or by a production method described in Japanese Patent No. 5972437 in which a slurry prepared using a volatile solvent is charged into a container and then the volatile solvent is removed.

The elastomer-coated organic powder can also be incorporated in a cosmetic by using the same production method as that for the inorganic powder.

According to the technique of the present invention, elastomer coating can be applied collectively to all of the inorganic powder (C) and the organic powder (D) to be incorporated in a cosmetic, and then other oil components can be added to obtain the cosmetic. Specifically, a cosmetic that has good in-use feel and high drop impact resistance was obtained by first mixing all of the inorganic powder and organic powder to be incorporated in the cosmetic, adding the elastomer-forming oil components to the resulting powder mixture, heating the powder mixture together with the elastomer-forming oil components to obtain an elastomer-coated powder mixture, and then adding oil components other than the components (A) and (B).

If a step of adding the elastomer-forming oil components (A) and (B) used in the technique of the present invention together with the other oil components and then performing heating is employed, the functions intended by the present invention cannot be obtained.

Specifically, when a cosmetic was obtained by mixing the inorganic powder and the organic powder to be incorporated in the cosmetic, then adding a mixture of the components (A) and (B) and the other oil components, and heating the resulting mixture, the obtained cosmetic was inferior in the in-use feel and drop impact resistance.

The oil components other than the components (A) and (B) can be incorporated without qualitative or quantitative limitations as long as the effect of the present invention is not impaired. A liquid oil, a solid oil, a wax, a hydrocarbon, a higher fatty acid, a higher alcohol, an ester, a silicone, a moisturizer, a water-soluble polymer, a thickener, a film former, an ultraviolet absorber, a metal sequestrant, a lower alcohol, a polyhydric alcohol, a sugar, an amino acid, an organic amine, a polymer emulsion, a pH adjuster, a nutritional supplement for skin, an antioxidant, an antioxidant synergist, and/or a flavor may be incorporated as necessary. The cosmetic can be produced by an ordinary method appropriate for the intended form of the cosmetic.

Examples of liquid fats include avocado oil, camellia oil, turtle oil, macadamia nut oil, corn oil, mink oil, olive oil, rapeseed oil, egg yolk oil, sesame oil, par chic oil, wheat germ oil, sasanqua oil, castor oil, linseed oil, safflower oil, cotton seed oil, perilla oil, soybean oil, groundnut oil, brown real oil, torreya oil, rice bran oil, Chinese wood oil, jojoba oil, germ oil, and triglycerol.

Examples of solid fats include cacao butter, coconut oil, horse fat, hydrogenated coconut oil, palm oil, beef fat, mutton suet, hydrogenated beef fat, palm kernel oil, lard, beef bones fat, Japan wax kernel oil, hardened oil, hoof oil, Japan wax, and hydrogenated castor oil.

Examples of waxes include beeswax, candelilla wax, cotton wax, carnauba wax, bayberry wax, insect wax, spermaceti, montan wax, bran wax, lanolin, kapok wax, lanolin acetate, liquid lanolin, sugarcane wax, lanolin fatty acid isopropyl, hexyl laurate, reduced lanolin, jojoba wax, hard lanolin, shellac wax, POE lanolin alcohol ether, POE lanolin alcohol acetate, POE cholesterol ether, lanolin fatty acid polyethylene glycol, POE hydrogenated lanolin alcohol ether and cetyl palmitate.

Examples of hydrocarbon oils include liquid paraffin, ozocerite, squalene, pristane, paraffin, ceresin, squalane, Vaseline, and microcrystalline wax.

Examples of the higher fatty acid include lauric acid, myristic acid, palmitic acid, stearic acid, behenic acid, oleic acid, undecylenic acid, tall oil acid, isostearic acid, linoleic acid, linolenic acid, eicosapentaenoic acid (EPA), docosahexaenoic acid (DHA).

Examples of higher alcohols include linear alcohol (for example, lauryl alcohol, cetyl alcohol, stearyl alcohol, behenyl alcohol, myristyl alcohol, oleyl alcohol, and cetostearyl alcohols); branched-chain alcohols (for example, monostearylglycerin ether (batyl alcohol), 2-decyltetradecinol, lanolin alcohol, cholesterol, phytosterol, hexyldodecanol, isostearyl alcohol, and octyldodecanol).

Examples of oils include isopropyl myristate, cetyl octanoate, octyldodecyl myristate, isopropyl palmitate, butyl stearate, hexyl laurate, myristyl myristate, decyl oleate, hexyldecyl dimethyl octanoate, cetyl lactate, myristyl lactate, lanolin acetate, isocetyl stearate, isocetyl isostearate, cholesteryl 12-hydroxy stearate, ethylene glycol di-2-ethyl hexanoate, di-penta erythritol fatty acid ester, N-alkyl glycol monoisostearate, neopentyl glycol dicaprate, diisostearyl malate, glycerol di-2-heptyl undecanoate, trimethyrol propane tri-2-ethyl hexanoate, trimethyrol propane triisostearate, tetra-2-ethyl hexanoate pentaerythritol, glycerol tri-2-ethyl hexanoate, glycerol trioctanoate, glycerol triisopalmitate, trimethyrol propane triisostearate, cetyl 2-ethylhexanoate, 2-ethylhexyl palmitate, glycerol trimyristate, glyceride tri-2-heptyl undecanoate, castor oil fatty acid methyl ester, oleyl oleate, acetoglyceride, 2-heptylundecyl palmitate, diisobutyl adipate, N-lauroyl-L-glutamic acid-2-octyldodecyl ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, and triethyl citrate.

Examples of the silicone oil include chain polysiloxanes (e.g., dimethyl polysiloxane, methylphenyl polysiloxane, and diphenyl polysiloxane); cyclic polysiloxanes (e.g., octamethylcyclotetrasiloxane, decamethylcyclopentasiloxane, and dodecamethylcyclohexasiloxane), silicone resins having a three-dimensional network, silicone rubbers, various modified polysiloxanes (amino-modified polysiloxane, polyether-modified polysiloxane, alkyl-modified polysiloxane, and fluorine-modified polysiloxane), and acrylic silicones.

Examples of moisturizers include polyethylene glycol, propylene glycol, glycerin, 1,3-butylene glycol, xylitol, sorbitol, maltitol, chondroitin sulfate, hyaluronic acid, mucoitin sulfate, charonic acid, atelocollagen, sodium lactate, bile salts, dl-pyrrolidone carboxylates, short-chain soluble collagen, diglycerin (EO)PO adduct, chestnut rose extract, yarrow extract, and melilot extract.

Examples of ultraviolet light absorbers include benzoic acid family ultraviolet light absorbers (for example, p-aminobenzoic acid (hereinafter abbreviated as PABA), PABA monoglycerine ester, N,N-dipropoxy PABA ethyl ester, N,N-diethoxy PABA ethyl ester, N,N-dimethyl PABA ethyl ester, N,N-dimethyl PABA butyl ester, and N,N-dimethyl PABA ethyl ester); anthranilic acid family ultraviolet light absorbers (for example, homomenthyl N-acetylanthranilate); salicylic acid family ultraviolet light absorbers (for example, amyl salicylate, menthyl salicylate, homomenthyl salicylate, octyl salicylate, phenyl salicylate, benzyl salicylate, and p-isopropanolphenyl salicylate); cinnamic acid family ultraviolet light absorbers (for example, octyl cinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxycinnamate, ethyl α-cyano-β-phenylcinnamate, 2-ethylhexyl α-cyano-β-phenylcinnamate, and glyceryl mono-2-ethylhexanoyl-diparamethoxy cinnamate); benzophenone family ultraviolet light absorbers (for example, 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone, and 4-hydroxy-3-carboxybenzophenone); 3-(4'-methylbenzylidene)-d,l-camphor, 3-benzylidene-d,l-camphor; 2-phenyl-5-methylbenzoxazol; 2,2'-hydroxy-5-methylphenylbenzotriazol; 2-(2'-hydroxy-5'-t-octylphenyl) benzotriazol, 2-(2'-hydroxy-5'-methylphenylbenzotriazol; dibenzalazine; dianisoylmethane; 4-methoxy-4'-t-butyldibenzoylmethane; and 5-(3,3-dimethyl-2-norbornylidene)-3-pentane-2-one.

Specific examples include glyceryl tri-2-ethylhexanoate and sorbitan sesquiisostearate.

The cosmetic containing the elastomer-coated inorganic powder of the present invention can, as necessary, contain water, a powder other than the powders mentioned above, a surfactant, a lower alcohol, a polyhydric alcohol, a moisturizer, a preservative, a polymer (including a film former), an antioxidant, a flavor, and/or other various agents in addition to the elastomer-coated inorganic powder, without qualitative or quantitative limitations as long as the effect of the present invention is not impaired.

The above-described cosmetic can be in any form, for example, foundation, eye shadow, teak, sunscreen, lotion, essence, puck, cleansing cream, cleansing foam, hand cream, shampoo and rinse.

EXAMPLES

Hereinafter, the present invention will be described in detail with reference to Examples. The present invention is not limited by these Examples in any respect. The amounts of components to be incorporated are expressed by % by mass relative to the entire system in which the components are incorporated, unless otherwise specified.

Evaluation methods and criteria used in the following test will be described first.

<Elastomer Coating Test>

In this test, no separation between the original powder and the elastomer was confirmed based on visual inspection and feel to the touch. Additionally, it was also confirmed that the amount of the elastomer was appropriate relative to the amount of the powder charged by elemental analysis and that the coating was appropriate by floating the coated powder on water to check whether it had water repellency.

G (good): The powder is coated with the elastomer.

NG (not good): The powder is not coated with the elastomer.

First, an investigation was conducted on the amounts of the amino group-containing silicone polymer (A) and the carboxyl group-containing silicone polymer (B) to obtain a composition according to the present invention in the form of an elastomer.

Elastomers according to the present invention which had formulations as shown in tables below were prepared by the following production method.

<Production Method>

Each of the elastomers according to the present invention was obtained by mixing and stirring the carboxyl group-containing silicone polymer and the amino group-containing silicone polymer and heating the mixture at 105° C. for 12 hours.

First, the present inventors conducted an investigation on the molar ratio Y/X at which the amino group-containing silicone polymer (A) and the carboxyl group-containing silicone polymer (B) exhibit elastomeric properties, wherein Y denotes the molar amount of carboxyl groups contained in the component (B), and X denotes the molar amount of amino groups contained in the component (A). The ratio Y/X is the ratio [amount (mmol) of carboxyl group]/[amount (mmol) of amino group] calculated from the carboxyl group equivalent and diamino group equivalent determined by NMR.

The formulations of the Test Examples are as shown in Table 1 and Table 2 below.

TABLE 1

| Test Example | | 1-1 | 1-2 | 1-3 | 1-4 | 1-5 | 1-6 |
|---|---|---|---|---|---|---|---|
| (A) | Aminoethylaminopropylmethylsiloxane-dimethylsiloxane copolymer (g) (*1) | 2 | 1.8 | 1.6 | 1.4 | 1.2 | 1 |
| (B) | PCA dimethicone (g) (*2) | — | 0.2 | 0.4 | 0.6 | 0.8 | 1 |
| mol B/mol A | | | 0.03 | 0.07 | 0.12 | 0.18 | 0.27 |
| mol A: Molar amount of amine, mol B: Molar amount of carboxylic acid (calculated from NMR data) | | | | | | | |
| State | | | Liquid | | | Elastomer | |

TABLE 2

| Test Example | | 1-7 | 1-8 | 1-9 | 1-10 | 1-11 |
|---|---|---|---|---|---|---|
| (A) | Aminoethylaminopropylmethylsiloxane-dimethylsiloxane copolymer (*1) | 0.8 | 0.6 | 0.4 | 0.2 | — |
| (B) | PCA dimethicone (*2) | 1.2 | 1.4 | 1.6 | 1.8 | 2 |
| mol B/mol A | | 0.41 | 0.64 | 1.1 | 2.5 | |
| mol A: Molar amount of amine, mol B: Molar amount of carboxylic acid (calculated from NMR data) | | | | | | |
| State | | | Elastomer | | Liquid | |

(*1) KF-8004 (Shin-Etsu Chemical Co., Ltd.)
$^1$H-NMR of KF-8004 was measured, and the diamine equivalent was calculated to be 3090.4 g/mol from an integral of a signal derived from $CH_3$ and an integral of a signal derived from $—CH_2—$.

(*2) SENSASIL PCA (Croda, Inc.)
$^1$H NMR of SENSASIL PCA was measured, and the carboxyl equivalent was calculated to be 5631 g/mol from an integral of a signal derived from $CH_3$ and an integral of a signal derived from $—CH_2—$.

It was found that elastomers were obtained by the formulations of Test Examples 1-4 to 1-9.

It was therefore found that the molar ratio Y/X between amino groups and carboxyl groups of 0.1 to 1.2 was advantageous.

Next, the present inventors conducted an investigation on whether a carboxyl group-containing acrylamide polymer could alternatively be used as another component (B).

methanol. The azobisisobutyronitrile was recrystallized from methanol according to an ordinary method before use.

The solution was degassed by bubbling with argon for 60 minutes, after which the container containing the solution was capped with a septum and heated at 60° C. for 20 hours to allow polymerization to proceed. After the completion of the polymerization reaction, the reaction solution was added dropwise into a largely excessive amount of diethyl ether, and the resulting precipitate was collected by suction filtration.

The collected precipitate was then dried under reduced pressure to give 15.2 g of a COOH-containing acrylamide polymer in the form of a random copolymer (yield; 75.1%). The weight-average molecular weight of the COOH-containing acrylamide polymer obtained was 50000.

This led to the conclusion that an elastomer according to the present invention could be obtained also with the use of a carboxyl group-containing acrylamide polymer.

TABLE 3

| Test Example | | 2-1 | 2-2 | 2-3 | 2-4 | 2-5 | 2-6 | 2-7 | 2-8 |
|---|---|---|---|---|---|---|---|---|---|
| (A) | Aminoethylaminopropylmethylsiloxane-dimethylsiloxane copolymer (*1) | 1 | 1 | 1 | 1 | 1 | 1 | 1 | 1 |
| (B) | COOH-containing acrylamide polymer (*3) | 1 | 0.5 | 0.33 | 0.25 | 0.2 | 0.17 | 0.13 | 0.1 |
| mol B/mol A | | 5.0 | 2.5 | 1.7 | 1.3 | 1.0 | 0.8 | 0.6 | 0.5 |
| mol A: Molar amount of amine, mol B: Molar amount of carboxylic acid (calculated from NMR data) | | | | | | | | | |
| State | | | | Hard solid | | | Elastomer | | |

(*3) The COOH-containing acrylamide polymer was obtained by the following method.

12-Methacrylamidododecanoic acid (MAD)/2-acrylamido-2-methylpropanesulfonic acid (AMPS) copolymer (90/10)

18.50 g (65.37 mmol) of 12-methacrylamidododecanoic acid (MAD), 1.50 g (7.24 mmol) of 2-acrylamido-2-methylpropanesulfonic acid (AMPS, available from Sigma-Aldrich Japan K.K.), 0.29 g (7.25 mmol) of sodium hydroxide, and 0.30 g (1.83 mmol) of azobisisobutyronitrile (available from Nacalai Tesque, Inc.) were dissolved in 60.0 g of <Elastomer-Coated Inorganic Powder>
As described hereinafter, the present inventors further conducted an investigation on whether various inorganic powders (C) could be coated with an elastomer according to the present invention.

<Production Method>
An inorganic powder (C) and a carboxyl group-containing silicone polymer are placed in a Henschel mixer and mixed at a low speed for 10 minutes. An amino group-containing silicone polymer was then added, followed by mixing at a low speed for 10 minutes and then by heating. In this manner, an elastomer-coated inorganic powder according to the present invention was obtained.

TABLE 4

| | Test Example | 3-1 | 3-2 | 3-3 |
|---|---|---|---|---|
| (A) | Aminoethylaminopropylmethylsiloxane-dimethylsiloxane copolymer (g) (*1) | 2 | 2 | 2 |
| (B) | PCA dimethicone (g) (*2) | 3 | 3 | 3 |
| (C) | Talc | 95 | — | — |
| | Mica | — | 95 | — |
| | Synthetic phlogopite iron | — | — | 95 |
| Coating state | | G | G | G |

Various Inorganic Powders Listed in Table 4

Talc: Talc JA-68R (available from ASADA MILLING CO., LTD.)

Mica: PDM-9WA (available from TOPY INDUSTRIES, LTD.)

Synthetic phlogopite iron: PDM-FE (available from TOPY INDUSTRIES, LTD.)

Test Examples 3-1 to 3-4 demonstrated that an elastomer according to the present invention could be used to coat various inorganic powders (C).

<Elastomer-Coated Inorganic Powder-Containing Cosmetic>

The present inventors conducted an investigation on the incorporation of an elastomer-coated inorganic powder according to the present invention in a cosmetic.

<Drop Test>

Each of the compositions of Test Examples was dropped from a height of 30 cm five times, and breakage of the formulation was evaluated according to the following criteria.

G (good): Not broken
NG (not good): Broken

<In-Use Feel>

Ten experienced panelists evaluated the in-use feel of each of the compositions of Test Examples by comprehensively considering the non-powderiness, lightness, smoothness, good fit, and skin compatibility that the panelists felt when placing the composition on their palm and applying it to their skin. The compositions were rated according to the following criteria.

A: Nine or more of the ten panelists reported that the in-use feel was good.

B: Six or more and less than nine of the ten panelists reported that the in-use feel was good.

C: Three or more and less than six of the ten panelists reported that the in-use feel was good.

D: Less than three of the ten panelists reported that the in-use feel was good.

<Dry Method of Producing Elastomer-Coated Inorganic Powder-Containing Cosmetic>

Powder components, oil components, and other components, which are shown in the following formulations, were first mixed using a Henschel mixer, and the mixture was then crushed twice using a pulverizer. The resulting mixture was charged into a middle-sized dish made of resin and subjected to dry press forming according to a known method. In this manner, a solid powder cosmetic was obtained.

Subsequently, the present inventors conducted the investigations on the in-use feel and drop impact stability of the cosmetics containing the elastomer-coated inorganic powder according to the present invention.

TABLE 5

| Test Example | 4-1 | 4-2 | 4-3 | 4-4 |
|---|---|---|---|---|
| Talc (*4) | 40 | — | — | — |
| Talc treated with calcium stearate (*6) | — | 40 | — | — |
| Talc treated with silicone elastomer (*7) | — | — | 40 | 40 |
| Synthetic phlogopite (*10) | Rest | Rest | Rest | — |
| Synthetic phlogopite treated with silicone elastomer | — | — | — | Rest |
| Titanium oxide treated with alkyl-modified silicone (*11) | 6 | 6 | 6 | 6 |
| Colcothar treated with alkyl-modified silicone (*13) | 1.00 | 1.00 | 1.00 | 1.00 |
| Iron oxide (yellow) treated with alkyl-modified silicone (*14) | 3.00 | 3.00 | 3.00 | 3.00 |
| Iron oxide (black) treated with alkyl-modified silicone (*15) | 0.1 | 0.1 | 0.1 | 0.1 |
| Silicic anhydride (*16) | 3 | 3 | 3 | 3 |
| Methyl methacrylate crosspolymer (*17) | 9 | 9 | 9 | 9 |
| Glyceryl tri-2-ethylhexanoate (*20) | 7 | 7 | 7 | 7 |
| Sorbitan sesquiisostearate (*22) | 1 | 1 | 1 | 1 |
| Total | 100.00 | 100.00 | 100.00 | 100.00 |
| Drop | D | B | B | B |
| In-use feel | C | B | A | A |

(*4) Talc JA-68R (available from ASADA MILLING CO., LTD.)

(*6) Talc ACS-515 (available from FUJIMOTO CHEMICALS CO., LTD.)

(*7) Elastomer-treated talc (Talc JA-68R (A: 2%, B: 3%))

(*10) PDM-9WA (available from TOPY INDUSTRIES, LTD.)

(*11) EP1-CR-50P (available from Daito Kasei Kogyo Co., Ltd.)

(*13) EP1-colcothar #216P (available from Daito Kasei Kogyo Co., Ltd.)

(*14) EP1-ocher #1P (available from Daito Kasei Kogyo Co., Ltd.)

(*15) EP1-BL-100P (available from Daito Kasei Kogyo Co., Ltd.)

(*16) SUNSPHERE L-51S (available from AGC Si-Tech Co., Ltd.)

(*17) MICROSPHERE M-306 (available from Matsumoto Yushi-Seiyaku Co., Ltd.)

(*21) RA-G-308 (available from Nippon Fine Chemical Co., Ltd.)

(*22) ESTEMOL 182V (available from The Nisshin OilliO Group, Ltd.)

Synthetic phlogopite treated with silicone elastomer (PDM-FEA: 2%, B: 3%))

From Test Examples 4-1 to 4-3, the present inventors found that when an elastomer-coated inorganic powder of the present invention was incorporated in a cosmetic, the resulting cosmetic had very excellent in-use feel and drop impact stability.

From Test Example 4-4, it was found that also when an elastomer-coated inorganic powder prepared using an inorganic powder other than talc as a core material was incorporated in a cosmetic, the resulting cosmetic had excellent in-use feel and drop impact stability.

The present inventors conducted an investigation on a cosmetic obtained using a carboxyl group-containing acrylamide polymer as another component (B).

TABLE 6

| Test Example | 5-1 |
|---|---|
| Talc treated with acrylamide-silicone elastomer (*7) | 40 |
| Synthetic phlogopite (*10) | Rest |
| Titanium oxide treated with alkyl-modified silicone (*11) | 6 |
| Colcothar treated with alkyl-modified silicone (*13) | 1.00 |
| Iron oxide (yellow) treated with alkyl-modified silicone (*14) | 3.00 |
| Iron oxide (black) treated with alkyl-modified silicone (*15) | 0.1 |
| Silicic anhydride (*16) | 3 |
| Methyl methacrylate crosspolymer (*17) | 9 |
| Glyceryl tri-2-ethylhexanoate (*20) | 7 |
| Sorbitan sesquiisostearate (*22) | 1 |
| Total | 100.00 |
| Falling (Drop) | B |
| In-use fee | A |

(*7) Talc treated with acrylamide-silicone elastomer (Talc JA-68R, (A): 4.5%, (B): 0.5%)

As seen from Test Example 5-1, it was found that also when an inorganic powder coated with an elastomer formed with the use of a carboxyl group-containing acrylamide polymer was incorporated in a cosmetic, the resulting cosmetic had very excellent in-use feel and drop impact stability.

Further, the present inventors conducted an investigation on whether, when an inorganic powder (C) was coated only with a component (A) or component (B) and the coated inorganic powder was incorporated in a cosmetic, the resulting cosmetic could exhibit the effect of the present invention.

TABLE 7

| Test Example | 6-1 | 6-2 | 6-3 | 6-4 |
|---|---|---|---|---|
| Talc (*4) | 40 | — | — | — |
| Talc treated with aminoethylaminopropylmethylsiloxane-dimethylsiloxane copolymer (*1) | — | 40 | — | — |
| Talc treated with PCA dimethicone (*2) | — | — | 40 | — |
| Talc treated with silicone elastomer (*7) | — | — | — | 40 |
| Synthetic phlogopite (*10) | Rest | Rest | Rest | Rest |
| Titanium oxide treated with alkyl-modified silicone (*11) | 6 | 6 | 6 | 6 |
| Colcothar treated with alkyl-modified silicone (*13) | 1.00 | 1.00 | 1.00 | 1.00 |
| Iron oxide (yellow) treated with alkyl-modified silicone (*14) | 3.00 | 3.00 | 3.00 | 3.00 |
| Iron oxide (black) treated with alkyl-modified silicone (*15) | 0.1 | 0.1 | 0.1 | 0.1 |
| Silicic anhydride (*16) | 3 | 3 | 3 | 3 |
| Methyl methacrylate crosspolymer (*17) | 9 | 9 | 9 | 9 |
| Glyceryl tri-2-ethylhexanoate (*20) | 7 | 7 | 7 | 7 |
| Sorbitan sesquiisostearate (*22) | 1 | 1 | 1 | 1 |
| Total | 100.00 | 100.00 | 100.00 | 100.00 |
| Falling | B | D | D | B |
| In-use feel | C | B | C | A |

These Test Examples demonstrated that when an inorganic powder (C) coated only with a component (A) or component (B) was incorporated in a cosmetic, the resulting cosmetic could not exhibit the effect of the present invention.

Further, the present inventors conducted an investigation on the order in which the elastomer-forming oil components including the amino group-containing silicone polymer (A) and the carboxyl group-containing silicone polymer (B), the inorganic powder (C), and other oil components were mixed to obtain a cosmetic containing an elastomer-coated inorganic powder according to the present invention.

TABLE 8

| | Test Example | 7-1 | 4-3 |
|---|---|---|---|
| | Talc treated with silicone elastomer | — | 40 |
| (A) | Amino-modified silicone | 1.8 | — |
| (B) | Pyrrolidone carboxylic acid-modified silicone | 2.7 | — |
| (C) | Talc (*4) | 40 | — |
| | Synthetic phlogopite (*10) | Rest | Rest |
| | Titanium oxide treated with alkyl-modified silicone (*11) | 6 | 6 |
| | Colcothar treated with alkyl-modified silicone (*13) | 1 | 1 |
| | Iron oxide (yellow) treated with alkyl-modified silicone (*14) | 3 | 3 |
| | Iron oxide (black) treated with alkyl-modified silicone (*15) | 0.1 | 0.1 |
| | Silicic anhydride (*16) | 3 | 3 |
| (D) | Methyl methacrylate crosspolymer (*17) | 9 | 9 |
| Oil component | Glyceryl tri-2-ethylhexanoate (*20) | 5 | 7 |
| | Sorbitan sesquiisostearate (*22) | 1 | 1 |
| | Total | 100 | 100 |
| Evaluation | Falling | B | B |
| | In-use feel | A | A |

In Test Example 7-1, the inorganic powders (C) including talc to silicic anhydride were mixed with the organic powder (D) using a Henschel mixer, and the amino-modified silicone (A) was then added, followed by mixing using the Henschel mixer.

The pyrrolidone carboxylic acid-modified silicone (B) was further added, followed by mixing using the Henschel mixer. The resulting mixture was then collected into a tray and heated at 105° C. for 12 hours to obtain an elastomer-treated powder mixture.

The elastomer-treated powder mixture and the other oil components were mixed using a Henschel mixer, and the resulting mixture was then crushed twice using a pulverizer.

The resulting powder was charged into a middle-sized dish made of resin and subjected to dry press forming according to a known method. In this manner, a solid powder cosmetic was obtained.

According to the present invention, elastomer coating can be applied collectively to all of the inorganic powder (C) and the organic powder (D) to be incorporated in a cosmetic, and then other oil components can be added to obtain the cosmetic. Specifically, a cosmetic that has good in-use feel and high drop impact resistance was obtained by first mixing all of the inorganic powder and organic powder to be incorporated in the cosmetic, adding the elastomer-forming oil components to the resulting powder mixture, heating the powder mixture together with the elastomer-forming oil components to obtain an elastomer-coated powder mixture, and then adding oil components other than the components (A) and (B) (Test Example 7-1).

TABLE 9

| | Test Example | 7-2 | 4-3 |
|---|---|---|---|
| | Talc treated with silicone elastomer | — | 40 |
| (A) | Amino-modified silicone | 0.8 | — |
| (B) | Pyrrolidone carboxylic acid-modified silicone | 1.2 | — |
| (C) | Talc (*4) | 38 | — |
| | Synthetic phlogopite (*10) | Rest | Rest |
| | Titanium oxide treated with alkyl-modified silicone (*11) | 6 | 6 |
| | Colcothar treated with alkyl-modified silicone (*13) | 1 | 1 |
| | Iron oxide (yellow) treated with alkyl-modified silicone (*14) | 3 | 3 |
| | Iron oxide (black) treated with alkyl-modified silicone (*15) | 0.1 | 0.1 |
| | Silicic anhydride (*16) | 3 | 3 |
| (D) | Methyl methacrylate crosspolymer (*17) | 9 | 9 |
| Oil component | Glyceryl tri-2-ethylhexanoate (*20) | 5 | 7 |
| | Sorbitan sesquiisostearate (*22) | 1 | 1 |
| | Total | 100 | 100 |
| Evaluation | Falling | D | B |
| | In-use feel | C/B | A |

In Test Example 7-2, the inorganic powders (C) including talc to silicic anhydride are placed and mixed in a Henschel mixer. The elastomer-forming oil components (A) and (B) and the other oil components were mixed in advance, and the mixture was added into the Henschel mixer, the contents of which were mixed and stirred. The resulting mixture was crushed twice using a pulverizer. The resulting powder was charged into a middle-sized dish made of resin and subjected to dry press forming according to a known method. In this manner, a solid powder cosmetic was obtained.

If a step of adding the elastomer-forming oil components (A) and (B) used in the technique of the present invention together with the other oil components and then performing heating is employed, the functions intended by the present invention cannot be obtained. Specifically, when a cosmetic was obtained by mixing the inorganic powder and the organic powder to be incorporated in the cosmetic, then adding a mixture of the components (A) and (B) and the other oil components, and heating the resulting mixture, the obtained cosmetic was inferior in the in-use feel and drop impact resistance (Test Example 7-2).

Examples of formulations employed when other inorganic powders (C) coated with an elastomer were incorporated in solid powder cosmetics are listed below.

TABLE 10

| Formulation Example | 1-1 | 1-2 | 1-3 | 1-4 |
|---|---|---|---|---|
| Talc treated with silicone elastomer (*7) | 40 | 40 | 40 | 40 |
| Synthetic phlogopite (*10) | — | Rest | Rest | Rest |
| Synthetic phlogopite iron treated with silicone elastomer | Rest | — | — | — |
| Boron nitride treated with silicone elastomer | — | 5 | — | — |
| Barium sulfate treated with silicone elastomer | — | — | 5 | — |
| Titanium oxide treated with alkyl-modified silicone (*11) | 6 | 6 | 6 | — |
| Colcothar treated with alkyl-modified silicone (*13) | 1.00 | 1.00 | 1.00 | — |
| Iron oxide (yellow) treated with alkyl-modified silicone (*14) | 3.00 | 3.00 | 3.00 | — |
| Iron oxide (black) treated with alkyl-modified silicone (*15) | 0.1 | 0.1 | 0.1 | 0.1 |
| Titanium oxide treated with silicone elastomer | | | | 6 |
| Iron oxide (red) treated with silicone elastomer | | | | 1 |
| Iron oxide (yellow) treated with silicone elastomer | | | | 3 |
| Zinc oxide treated with silicone elastomer | | | | 3 |
| Silicic anhydride (*16) | 3 | 3 | 3 | 3 |
| Methyl methacrylate crosspolymer (*17) | 9 | 9 | 9 | 9 |
| Glyceryl tri-2-ethylhexanoate (*20) | 7 | 7 | 7 | 7 |
| Sorbitan sesquiisostearate (*22) | 1 | 1 | 1 | 1 |
| Total | 100.00 | 100.00 | 100.00 | 100.00 |

<Other Methods of Producing Elastomer-Coated Inorganic Powder-Containing Cosmetic>

An investigation was conducted on whether a solid powder cosmetic containing an elastomer-coated inorganic powder of the present invention could be produced by a production method described in Japanese Patent No. 5422092 in which a slurry prepared using a volatile solvent is dried or by a production method described in Japanese Patent No. 5972437 in which a slurry prepared using a volatile solvent is charged into a container and then the volatile solvent is removed.

Example of Production Method in which Slurry is Dried

The powder components, oil components, and other components, listed below as the formulation A, were mixed first using a Henschel mixer, and the mixture was then crushed twice using a pulverizer. The crushed powder was added to ethyl alcohol, and the powder and ethyl alcohol were mixed using a dispersion mixer. The mixture was subjected to crushing, grinding, and dispersing using a stirred media mill (sand grinder mill) packed with 2-mm-diameter zirconia beads. As a result, a slurry was obtained. The slurry was dried in the form of fine droplets using a stirring dryer (spin flash dryer, available from APV Nordic Anhyro) to obtain a dry powder. The obtained dry powder was charged into a middle-sized dish made of resin and subjected to dry press forming according to a known method. In this manner, a solid powder cosmetic was obtained.

TABLE 11

| Formulation A | |
|---|---|
| Talc treated with silicone elastomer | Rest |
| Barium sulfate | 20 |

TABLE 11-continued

| Formulation A | |
|---|---|
| Sericite treated with silicone elastomer | 20 |
| Synthetic phlogopite treated with silicone elastomer | 5 |
| Synthetic phlogopite | 5 |
| Zinc myristate | 2 |
| Boron nitride | 1 |
| Titanium oxide treated with silicone | 11 |
| Iron oxide (red) treated with silicone | 0.5 |
| Iron oxide (yellow) treated with silicone | 2.5 |
| Iron oxide (black) treated with silicone | 0.1 |
| Spherical silicone elastomer powder | 5 |
| Spherical nylon powder | 5 |
| Vaseline | 1 |
| Squalane | 2 |
| Diisostearyl malate | 1 |
| Octyl methoxycinnamate | 1 |
| Dimethicone | 1 |
| Sorbitan sesquiisostearate | 0.5 |
| Preservative | Appropriate amount |
| Antioxidant | Appropriate amount |
| Flavor | Appropriate amount |
| Total | 100.00 |

Example of Production Method in which Slurry is Charged into Container and then Solvent is Removed The powder components and oil components, listed below as the formulation B, were mixed using a Henschel mixer, and the mixture was then crushed twice using a pulverizer. To the resulting mixture was added an equivalent amount of water (=volatile dispersion medium), and this was followed by mixing using a dispersion mixer to obtain a slurry. This slurry was charged into a middle-sized dish, and the solvent was removed by suction, followed by drying. In this manner, a solid powder cosmetic was obtained.

TABLE 12

| Formulation B | |
|---|---|
| Talc treated with silicone elastomer | 12.0 |
| Talc | 12.0 |
| Synthetic phlogopite | 10.0 |
| Synthetic phlogopite iron | 10.0 |
| Boron nitride | 5.0 |
| Titanium oxide treated with silicone (pigment grade) | 7.0 |
| Titanium dioxide treated with aluminum stearate (ultrafine particles) | 4.0 |
| Iron oxide (red) treated with silicone | 0.6 |
| Iron oxide (yellow) treated with silicone | 2.1 |
| Iron oxide (black) treated with silicone | 0.2 |
| Spherical silicone elastomer powder | 7.0 |
| Spherical nylon powder | 7.0 |
| Chlorphenesin | 0.1 |
| Dimethylpolysiloxane | 3.0 |
| Methylphenyl polysiloxane | 1.0 |
| Glyceryl tri-2-ethylhexanoate | 4.0 |
| Octyl methoxycinnamate | 5.0 |
| Total | 100% |

Cosmetics were suitably obtained both by the production method described in Japanese Patent No. 5422092 in which a slurry prepared using a volatile solvent is dried and by the production method described in Japanese Patent No. 5972437 in which a slurry prepared using a volatile solvent is charged into a container and then the volatile solvent is removed.

The following is an example of formulation employed when an inorganic powder (C) coated with an elastomer is incorporated in a solid powder cosmetic used as a solid eyeliner.

TABLE 13

| Formulation Example | 2-1 |
|---|---|
| Vaseline | 3 |
| Hydrogenated oil | 30 |
| Japan wax | 10 |
| Stearic acid | 12 |
| Trimethylolpropane trioctanoate | 5 |
| Titanium mica | 10 |
| Titanium oxide treated with silicone elastomer | 2 |
| Iron oxide (red) treated with silicone elastomer | 2 |
| Iron oxide (yellow) treated with silicone elastomer | 0.5 |
| Iron oxide (black) | 1 |
| Iron blue | 5 |
| Synthetic phlogopite treated with silicone elastomer | Rest |
| Total | 100.00 |

What is claimed is:

1. An elastomeric mixture of polymers, comprising:

(A) an amino group-containing silicone polymer represented by a general formula (1):

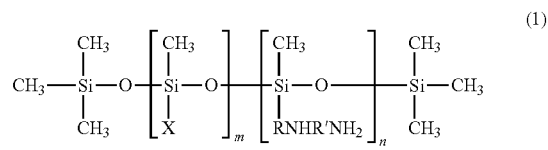

wherein X is an alkyl group having 1 to 18 carbons, and R and R' are an alkyl group; m is a number between 20 and 2000 and n is a number between 1 and 100;

(B) at least one polymer selected from a group consisting of a carboxyl group-containing silicone polymer wherein said silicone polymer is represented by a general formula (2):

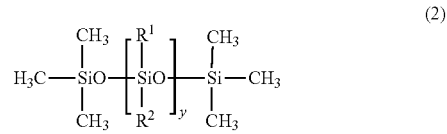

wherein $R^1$ and $R^2$ are selected from the group consisting of a methyl group and a group represented by formula (4), the total number of groups of formula (4) is 1 to 100 per molecule, and y represents an integer from 1 to 50000:

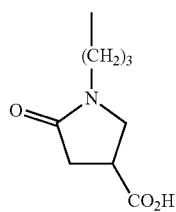

(4)

and (C) a polymer selected from carboxyl group-containing acrylamide polymers represented by a general formula (3):

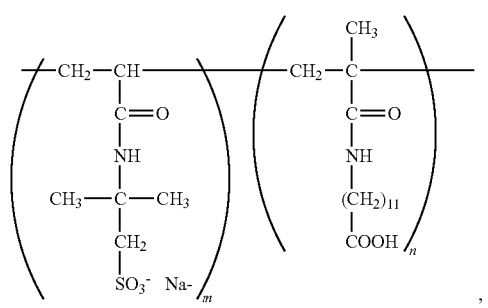

(3)

, wherein the molar ratio between amino groups of said (A) polymer and carboxyl groups of said (B) polymer in said elastomer, which is (mol B)/(mol A), is 0.1 to 1.2.

2. An elastomer-coated inorganic powder, wherein:

a surface of said inorganic powder is coated with the elastomeric mixture according to claim 1.

3. The elastomer-coated inorganic powder, according to claim 2, wherein:

the amount of the elastomeric mixture is in the range of 0.5 to 20% by mass relative to the amount of said inorganic powder.

4. The elastomer-coated inorganic powder, according to claim 2, wherein:

said inorganic powder is at least one inorganic powder selected from the group consisting of talc, mica, synthetic phlogopite iron, sericite, barium sulfate, kaolin, titanium oxide, zinc oxide, and iron oxide.

5. A cosmetic, comprising:

said elastomer-coated inorganic powder according to claim 2.

6. An elastomer-coated organic powder, wherein:

a surface of said organic powder is coated with the elastomeric mixture according to claim 1.

* * * * *